United States Patent
Sakamoto et al.

(10) Patent No.: US 10,582,710 B2
(45) Date of Patent: Mar. 10, 2020

(54) ARTHROPOD PEST CONTROL COMPOSITION AND METHOD FOR CONTROLLING ARTHROPOD PESTS

(75) Inventors: Emiko Sakamoto, Takarazuka (JP); Norihisa Sakamoto, Kasai (JP)

(73) Assignee: SUMITOMO CHEMICAL COMPANY, LIMITED, Chuo-ku, Tokyo (JP)

( * ) Notice: Subject to any disclaimer, the term of this patent is extended or adjusted under 35 U.S.C. 154(b) by 0 days.

(21) Appl. No.: 13/991,763

(22) PCT Filed: Dec. 26, 2011

(86) PCT No.: PCT/JP2011/080572
§ 371 (c)(1),
(2), (4) Date: Jul. 12, 2013

(87) PCT Pub. No.: WO2012/091157
PCT Pub. Date: Jul. 5, 2012

(65) Prior Publication Data
US 2013/0281458 A1     Oct. 24, 2013

(30) Foreign Application Priority Data
Dec. 27, 2010 (JP) ................. 2010-289614

(51) Int. Cl.
*A01N 43/707* (2006.01)
*A01N 43/56* (2006.01)
*A01N 43/08* (2006.01)

(52) U.S. Cl.
CPC ........... *A01N 43/707* (2013.01); *A01N 43/08* (2013.01); *A01N 43/56* (2013.01)

(58) Field of Classification Search
None
See application file for complete search history.

(56) References Cited

U.S. PATENT DOCUMENTS

| 2008/0293566 A1 | 11/2008 | Suty-Heinze et al. |
| 2009/0104145 A1 | 4/2009 | Hughes et al. |

(Continued)

FOREIGN PATENT DOCUMENTS

| CN | 1988803 A | 6/2007 |
| CN | 101203135 A | 6/2008 |

(Continued)

OTHER PUBLICATIONS

Decision of Refusal dated Dec. 9, 2014 in counterpart Japanese Patent Application No. 2010-289614 with translation.

(Continued)

*Primary Examiner* — Jeffrey S Lundgren
*Assistant Examiner* — Stephanie K Springer
(74) *Attorney, Agent, or Firm* — Sughrue Mion, PLLC

(57) ABSTRACT

Disclosed is an arthropod pest control composition having an excellent controlling effect on arthropod pests, which comprises an amide compound represented by formula (1):

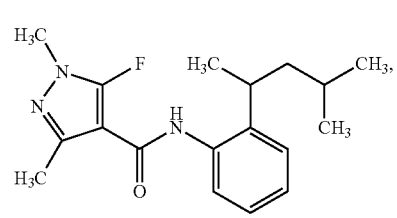

(1)

and an anthranilamide compound represented by formula (2):

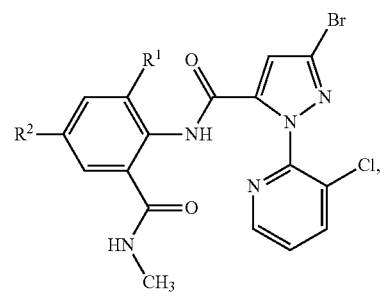

(2)

wherein a combination of $R^1$ and $R^2$ represents a combination wherein $R^1$ is a methyl group and $R^2$ is a chlorine atom, or a combination wherein $R^1$ is a methyl group and $R^2$ is a cyano group, and one or more Delphacidae control compounds selected from the following group (A):

Group (A): a group consisting of clothianidin, imidacloprid, thiamethoxam, dinotefuran, fipronil, pymetrozine, a compound represented by formula (I) and a compound represented by formula (II).

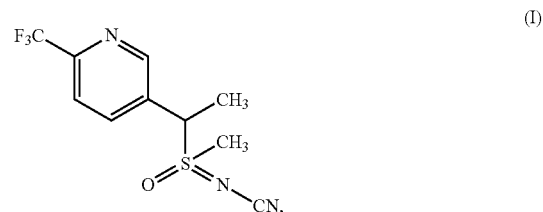

(I)

(Continued)

-continued

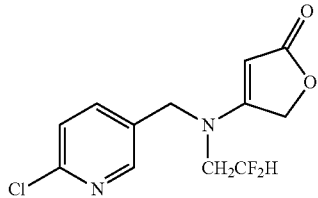

(II)

6 Claims, No Drawings

(56) References Cited

U.S. PATENT DOCUMENTS

| | | |
|---|---|---|
| 2010/0022389 A1 | 1/2010 | Langewald et al. |
| 2010/0034792 A1 | 2/2010 | Becker |
| 2010/0197737 A1 | 8/2010 | Hungenberg et al. |
| 2011/0124588 A1 | 5/2011 | Jeschke et al. |
| 2011/0319262 A1* | 12/2011 | Schade .................. A01N 47/40 504/100 |
| 2012/0004100 A1 | 1/2012 | Hungenberg et al. |
| 2012/0035050 A1 | 2/2012 | Jeschke et al. |

FOREIGN PATENT DOCUMENTS

| | | |
|---|---|---|
| CN | 101808522 A | 8/2010 |
| DE | 10 2005 022 147 A1 | 11/2006 |
| DE | 10 2007 045 922 A1 | 4/2009 |
| EP | 2100505 A1 | 9/2009 |
| JP | 2008-507582 A | 3/2008 |
| JP | 2008-539179 A | 11/2008 |
| JP | 2009-541339 A | 11/2009 |
| JP | 2010-503641 A | 2/2010 |
| KR | 1020090089388 A | 8/2009 |
| KR | 1020090108733 A | 10/2009 |
| WO | 2006/068669 A1 | 6/2006 |
| WO | 2007/149817 A2 | 12/2007 |
| WO | 2008/034785 A2 | 3/2008 |
| WO | 2008095870 A2 | 8/2008 |
| WO | 2009/043442 A1 | 4/2009 |
| WO | 2009/090181 A2 | 7/2009 |
| WO | 2009/135613 A1 | 11/2009 |
| WO | 2009147205 A2 | 12/2009 |
| WO | WO 2010040623 A1 * | 4/2010 ............. A01N 47/40 |
| WO | 2010/108507 A2 | 9/2010 |
| WO | 2010129345 A2 | 11/2010 |
| WO | 2012/084670 A1 | 6/2012 |
| WO | 2012/090911 A1 | 7/2012 |
| WO | 2013/008949 A1 | 1/2013 |

OTHER PUBLICATIONS

First Office Action Dated Jul. 2, 2014 in counterpart Chinese Patent Application No. 201180062512.5 with English translation.
Notification of Reason(s) for Rejection dated Sep. 16, 2014 in counterpart Japanese Patent Application No. 2010-289614 with translation.
Extended European Search Report dated May 22, 2014 in European Patent Application No. 11852401.6.
Lois Rossi: "Registration Application", Federal Register Volume Number, Jun. 16, 2010 (Jun. 16, 2010), pp. 34114-34115, XP055117829, Retrieved from the Internet: URL:http://digital.lobrary.unt.edu/ark:/67531/metadc52696/m1/140/ [retrieved on May 13, 2014].
International Preliminary Report on Patentability and Written Opinion dated Jul. 2, 2013 in International Application No. PCT/JP2011/080572.
The Pesticide Manual—15th edition (published by BCPC); ISBN 978-1-901396-18-8, pp. 174-175, 228-229, 250-251, 390-391, 500-501, 644-645, 968-969, and 1112-1113.
Second Office Action dated Feb. 17, 2015 in counterpart Chinese Patent Application No. 201180062512.5 with translation.
Communication dated Aug. 12, 2015 from the State Intellectual Property Office of the People's Republic of China in counterpart application No. 201180062512.5.
Communication dated Jul. 23, 2015 from the Taiwanese Intellectual Property Office in counterpart application No. 100148619.
Examination Report No. 1 dated Mar. 26, 2015 in counterpart Australian Patent Application No. 2011350400.
Office Action dated Apr. 20, 2017 in counterpart Taiwanese Patent Application No. 100148619 with English translation.
Office Action dated Apr. 20, 2017 in counterpart Taiwanese Patent Application No. 105115326 with English translation.
Communication dated Feb. 2, 2016 from the Japanese Patent Office issued in corresponding Application No. 2014-228657.
Communication dated Jun. 21, 2016, from the Indonesian Patent Office in counterpart application No. W00201303437.
Communication dated Nov. 30, 2015 from the Taiwan Patent Office in counterpart application No. 100148619.
Office Action dated Dec. 20, 2017 in counterpart Korean Patent Application No. 10-2013-7019609, with translation.
Communication dated Apr. 11, 2018, from the intellectual Property of India in counterpart application No. 5952/CHENP/2013.
Communication dated Apr. 11, 2018, issued by the Korean Intellectual Property Office in corresponding Korean Application No. 10-2013-7019609.
Communication dated Aug. 30, 2017 issued by the Mexican Patent Office in counterpart application No. MX/a/2013/006930.

* cited by examiner

ARTHROPOD PEST CONTROL COMPOSITION AND METHOD FOR CONTROLLING ARTHROPOD PESTS

CROSS REFERENCE TO RELATED APPLICATIONS

This application is a National Stage of International Application No. PCT/JP2011/080572 filed Dec. 26, 2011, claiming priority based on Japanese Patent Application No. 2010-289614 filed Dec. 27, 2010, the contents of all of which are incorporated herein by reference in their entirety.

TECHNICAL FIELD

The present application is filed claiming the priority of the Japanese Patent Application No. 2010-289614, the entire contents of which are herein incorporated by the reference.

The present invention relates to an arthropod pest control composition and a method for controlling arthropod pests.

BACKGROUND ART

Heretofore, various compounds are known as active ingredients in arthropod pest control compositions (see, for example, The Pesticide Manual-15th edition (published by BCPC); ISBN 978-1-901396-18-8).

SUMMARY OF INVENTION

Technical Problem

An object of the present invention is to provide an arthropod pest control composition having an excellent control effect on arthropod pests.

Solution to Problem

The present inventors have intensively studied for providing an arthropod pest control composition having an excellent control effect on arthropod pests, and finally found that a composition comprising an amide compound represented by the following formula (1), an anthranilamide compound represented by the following formula (2) and one or more Delphacidae control compounds selected from the following group (A) has an excellent control effect on arthropod pests, thereby attaining the present invention.

Namely, the present invention includes the followings [1] to [5]:

[1] An arthropod pest control composition comprising an amide compound represented by formula (1):

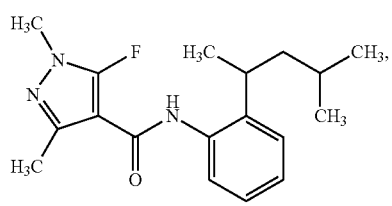

(1)

an anthranilamide compound represented by formula (2):

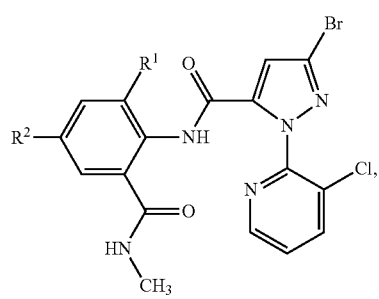

(2)

wherein a combination of $R^1$ and $R^2$ represents a combination wherein $R^1$ is a methyl group and $R^2$ is a chlorine atom, or a combination wherein $R^1$ is a methyl group and $R^2$ is a cyano group, and
one or more Delphacidae control compounds selected from the following group (A):
Group (A): a group consisting of clothianidin, imidacloprid, thiamethoxam, dinotefuran, fipronil, pymetrozine, a compound represented by formula (I) and a compound represented by formula (II).

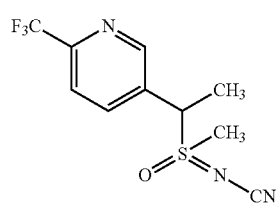

(I)

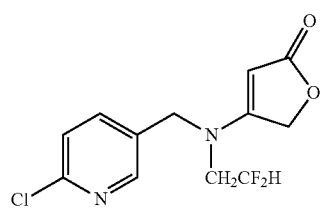

(II)

[2] The arthropod pest control composition according to the above [1], wherein the weight ratio of the amide compound to the anthranilamide compound is from 50:1 to 1:50.
[3] The arthropod pest control composition according to the above [2], wherein the weight ratio of the amide compound to the Delphacidae control compound is from 50:1 to 1:100.
[4] A method for controlling an arthropod pest, which comprises applying an effective amount of the arthropod pest control composition according to any one of the above [1] to [3] to a plant or an area in which a plant is grown.
[5] The method for controlling an arthropod pest according to the above [4], wherein the plant or the area in which a plant is grown is rice or area in which rice is grown.

Effects of Invention

According to the present invention, it is possible to control an arthropod pest.

DESCRIPTION OF EMBODIMENTS

The arthropod pest control composition of the present invention comprises an amide compound represented by the following formula (1) (hereinafter sometimes referred to as "the present amide compound"):

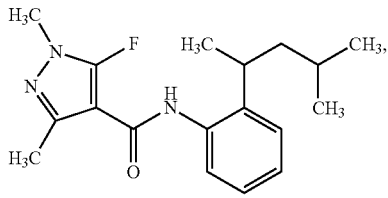

an anthranilamide compound represented by the following formula (2) (hereinafter sometimes referred to as "the present anthranilamide compound"):

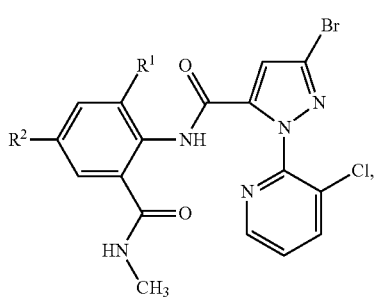

wherein a combination of $R^1$ and $R^2$ represents a combination wherein $R^1$ is a methyl group and $R^2$ is a chlorine atom, or a combination wherein $R^1$ is a methyl group and $R^2$ is a cyano group, and
one or more Delphacidae control compounds (hereinafter sometimes referred to as "the present Delphacidae control compound") selected from the following group (A).
Group (A): a group consisting of clothianidin, imidacloprid, thiamethoxam, dinotefuran, fipronil, pymetrozine, a compound represented by formula (I) (hereinafter referred to as "the present compound (I)") and a compound represented by formula (II) (hereinafter referred to as "the present compound (II)").

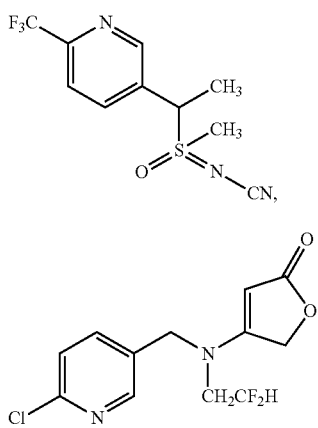

The present amide compound is known and can be prepared, for example, by a process described in WO 2003/010149.

Among the present anthranilamide compounds, a compound represented by formula (2) wherein $R^2$ is a methyl group and $R^2$ is a chlorine atom (hereinafter referred to as "the present anthranilamide compound (i)") is described, for example, at page 175 of "The Pesticide Manual-15th edition (published by BCPC); ISBN 978-1-901396-18-8". Said compound can be obtained from commercial sources or produced by a known method.

Among the present anthranilamide compounds, a compound represented by formula (2) wherein $R^1$ is a methyl group and $R^2$ is a cyano group (hereinafter referred to as "the present anthranilamide compound (ii)") is described, for example, at page 251 of "The Pesticide Manual-15th edition (published by BCPC); ISBN 978-1-901396-18-8", and can be produced by a method described in WO 2004/067528.

Clothianidin, imidacloprid, thiamethoxam, dinotefuran, fipronil and pymetrozine to be used in the present invention are known compounds, and described, for example, at pages 229, 645, 1112, 391, 500 and 968 of "The Pesticide Manual-15th edition (published by BCPC); ISBN 978-1-901396-18-8". These compounds can be obtained from commercial sources or produced by a known method.

The present compound (I) is a known compound, and can be obtained, for example, by a method described in WO 2007/095229.

The present compound (II) is a known compound, and can be obtained, for example, by a method described in WO 2007/115644.

In the arthropod pest control composition of the present invention, the weight ratio of the present amide compound, the present anthranilamide compound and the Delphacidae control compound is not particularly limited. However, the present anthranilamide compound is generally 0.2 to 50000 parts by weight, preferably 2 to 5000 parts by weight, relative to 100 parts by weight of the present amide compound. The Delphacidae control compound is generally 0.2 to 100000 parts by weight, preferably 2 to 10000 parts by weight, relative to 100 parts by weight of the present amide compound.

The arthropod pest control composition of the present invention may be prepared by simply mixing the present amide compound, the present anthranilamide compound and the present Delphacidae control compound, but generally by mixing the present amide compound, the present anthranilamide compound and the present Delphacidae control compound and an inert carrier, and if necessary, a surfactant and/or other formulation additives, and then formulating the mixture into a dosage form such as an oil solution, an emulsifiable concentrate, a suspension concentrate, a wettable powder, a water dispersible granule, a dust, or a granule.

Thus formulated arthropod pest control composition may be used directly, or after the addition of other inert ingredients, as an arthropod pest control agent.

The total amount of the present amide compound, the present anthranilamide compound and the Delphacidae control compound in the arthropod pest control composition of the present invention is generally 0.01 to 99% by weight, preferably 0.1 to 90% by weight, more preferably 0.5 to 70% by weight.

Examples of the solid carrier used for formulation of the arthropod pest control composition include fine powders or granules of minerals (e.g., kaolin clay, attapulgite clay, bentonite, montmorillonite, acidic white clay, pyrophyllite, talc, diatomaceous earth, and calicite), natural organic substances (e.g., corncob flour, and walnut shell flour), synthetic organic substances (e.g., urea), salts (e.g., calcium carbonate, and ammonium sulfate), and synthetic inorganic substances (e.g., synthetic hydrated silicon oxide).

Examples of the liquid carrier include aromatic hydrocarbons (e.g., xylene, alkylbenzene, and methyl naphthalene), alcohols (e.g., 2-propanol, ethylene glycol, propylene glycol, and ethylene glycol monoethyl ether), ketones (e.g., acetone, cyclohexanone, and isophorone), vegetable oils (e.g., soybean oil, and cotton oil), petroleum-based aliphatic hydrocarbons, esters, dimethylsulfoxide, acetonitrile, and water.

Examples of the surfactant include anionic surfactants (e.g., alkyl sulfate ester salts, alkylaryl sulfonates, dialkyl sulfosuccinates, polyoxyethyle alkylaryl ether phosphate ester salts, ligninsulfonates, and naphthalene sulfonate formaldehyde polycondensates), nonionic surfactants (e.g., polyoxyethylene alkylaryl ethers, polyoxyethylene alkylpolyoxypropylene block copolymers, and sorbitan fatty acid esters), and cationic surfactants (e.g., alkyl trimethyl ammonium salts).

Examples of the formulation additive include water-soluble polymers (e.g., polyvinyl alcohol, and polyvinyl pyrrolidone), polysaccharides [e.g., gum arabic, alginic acid and a salt thereof, CMC (carboxymethyl cellulose), and xanthane gum], inorganic substances (e.g., aluminum magnesium silicate, and alumina-sol), preservatives, colorants, and stabilizers [e.g. PAP (isopropyl acid phosphate), and BHT].

The arthropod pest control composition of the present invention can be used for protecting a plant from damage due to eating or sucking by an arthropod pest.

Examples of the arthropod pest on which the arthropod pest control composition of the present invention has controlling effect include as described below:

Hemiptera:

Delphacidae such as *Laodelphax striatellus, Nilaparvata lugens, Sogatella furcifera*; Deltocephalidae such as *Nephotettix cincticeps, Nephotettix virescens, Recilia dorsalis, Empoasca onukii*; Aphididae such as *Aphis gossypii, Myzus persicae, Brevicoryne brassicae, Aphis spiraecola, Macrosiphum euphorbiae, Aulacorthum solani, Rhopalosiphum padi, Toxoptera citricidus, Hyalopterus pruni, Eriosoma lanigerum*; Pentatomidae such as *Nezara antennata, Trigonotylus caelestialium, Graphosoma rubrolineatum, Eysarcoris lewisi, Riptortus clavetus, Leptocorisa chinensis, Eysarcoris parvus, Halyomorpha mista, Nezara viridula*, and *Lygus lineolaris*; Aleyrodidae such as *Trialeurodes vaporariorum, Bemisia tabaci, Dialeurodes citri*, and *Aleurocanthus spiniferus*; Coccoidea such as *Aonidiella aurantii, Comstockaspis perniciosa, Unaspis citri, Ceroplastes rubens, Icerya purchasi, Planococcus kraunhiae, Pseudococcus longispinis*, and *Pseudaulacaspis pentagona*; Tingidae; Cimicoidea such as *Cimex lectularius*; Psyllidae such as *Cacopsylla pyricola*; etc.

Lepidoptera:

Pyralidae such as *Chilo suppressalis, Tryporyza incertulas, Cnaphalocrocis medinalis, Notarcha derogata, Plodia interpunctella, Ostrinia furnacalis, Hellula undalis*, and *Pediasia teterrellus*; Noctuidae such as *Spodoptera litura, Spodoptera exigua, Pseudaletia separata, Sesamia inferens, Mamestra brassicae, Agrotis ipsilon, Plusia nigrisigna, Trichoplusia ni, Thoricoplusia* spp., *Heliothis* spp., and *Helicoverpa* spp.; Pieridae such as *Pieris rapae*; Tortricidae such as *Adoxophyes* spp., *Grapholita molesta, Leguminivora glycinivorella, Matsumuraeses azukivora, Adoxophyes orana fasciata, Adoxophyes honmai., Homona magnanima, Archips fuscocupreanus*, and *Cydia pomonella*; Gracillariidae such as *Caloptilia theivora*, and *Phyllonorycter ringoneella*; Carposimidae such as *Carposina niponensis*; Lyonetiidae such as *Lyonetia* spp.; Lymantriidae such as *Lymantria* spp., and *Euproctis* spp.; Yponomeutidae such as *Plutella xylostella*; Gelechiidae such as *Pectinophora gossypiella*, and *Phthorimaea operculella*; Arctiidae such as *Hyphantria cunea*; Tineidae such as *Tinea translucens*, and *Tineola bisselliella; Tuta absoluta*; etc.

Thysanoptera:

Thripidae such as *Frankliniella occidentalis, Thrips parmi, Scirtothrips dorsalis, Thrips tabaci, Frankliniella intonsa, Frankliniella fusca, Stenchaetothrips biformis, Haplothrips aculeatus*; etc.

Diptera:

Agromyzidae such as *Hylemya antiqua, Hylemya platura, Agromyza oryzae, Hydrellia griseola, Chlorops oryzae*, and *Liriomyza trifolii; Dacus cucurbitae, Ceratitis capitata*; etc.

Coleoptera:

*Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne*; etc.

Orthoptera:

*Gryllotalpa africana, Oxya yezoensis, Oxya japonica*; etc.

Among the above arthropod pests, preferred are Delphacidae; Deltocephalidae; Aphididae; Pentatomidae; *Lissorhoptrus oryzophilus, Oulema oryzae*, Pyralidae; Noctuidae, etc.

The arthropod pest control composition of the present invention may be used for controlling plant diseases such as diseases caused by *Rhizoctonia solani*.

The arthropod pest control composition of the present invention can be used in agricultural lands such as fields, paddy fields, dry fields, lawns, and orchards or nonagricultural lands. The arthropod pest control composition of the present invention can be also used for controlling a pest in an agricultural land, etc. in which "plant", etc. is grown.

Examples of the plant to which the arthropod pest control composition of the present invention can be applied include as described below:

Crops: corn, rice, wheat, barley, rye, oat, sorghum, cotton, soybean, peanut, buckwheat, sugar beet, rapeseed, sunflower, sugar cane, tobacco, etc.;

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, rape, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese basil, mint, basil, etc.), strawberry, sweat potato, yam, aroid, etc.;

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, oil palm, etc.;

Trees other than fruit trees: tea, mulberry, flowering trees (azalea, camellia, hydrangea, sasanqua, Japanese star anise, cherry, tulip tree, crape myrtle, orange osmanthus, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, spruce, elm, horse chestnut, etc.), coral tree, podocarpus, cedar, Japanese cypress, croton, *Euonymus japonicus*, *Photinia glabra*, etc.;

lawns: *Zoysia* (zoysiagrass, *Zoysia matrella*, etc.), Bermuda grasses (*Cynodon dactylon*, etc.), bent grasses (*Agrostis alba*, creeping bent grass, hiland bent, etc.), blueglasses (meadow grass, bird grass, etc.), fescue (tall fescue, chewings fescue, creeping red fescue, etc.), ryegrasses (darnel, rye grass, etc.), orchard grass, timothy grass, etc.;

Others: flowers (rose, carnation, chrysanthemum, prairie gentian, gypsophila, gerbera, marigold, salvia, petunia, verbena, tulip, aster, gentian, lily, pansy, cyclamen, orchid, convallaria, lavender, stock, ornamental cabbage, primula, poinsettia, gladiolus, cattleya, daisy, cymbidium, begonia, etc.), bio-fuel plants (Jatropha, safflower, camelina, switchgrass, Miscanthus, reed canary grass, giant reed, kenaf, cassava, willow, etc.), ornamental plants, etc.

Among the above plants, preferred are corn, wheat, rice, etc., and particularly preferred is rice.

The "plant" as used herein may be those having resistance, which is imparted by a genetic engineering technique or a cross-breeding method.

The arthropod pest control composition of the present invention can be applied to a plant or an area in which a plant is grown for controlling arthropod pests therein. The plant as used herein include the stems and leaves of plants, the flowers of plants, the fruits of plants, the seeds of plants, etc.

The method for controlling an arthropod pest of the present invention comprises applying an effective amount of the arthropod pest control composition of the present invention to a plant or an area in which a plant is grown.

In the method of the present invention, the present amide compound, the present anthranilamide compound and the Delphacidae control compound may be applied separately or sequentially.

The "effective amount of the arthropod pest control composition" as used herein means the total amount of the present amide compound, the present anthranilamide compound and the Delphacidae control compound, which is capable of exerting the controlling effect on an arthropod pest.

Examples of the application method include application to the stems and leaves of plants such as foliage application; application to the seeds of plants; and application to area in which plants are grown such as soil application and submerged application.

Specific examples of the application to the stems and leaves of plants such as foliage application in the present invention include application to the surface of cultivated plants such as ground application by using manual sprayers, power sprayers, boom sprayers or Pancle sprayers, or aerial application or spraying by using radio control helicopters, etc.

Specific examples of the application to the seeds of plants in the present invention include immersion treatment, spray coating treatment, dressing treatment, film coating treatment and pellet coating treatment.

Specific examples of the application to area in which plants are grown such as soil application and submerged application in the present invention include planting hole treatment, plant foot treatment, planting furrow treatment, planting row treatment, broadcast treatment, side row treatment, seedling box treatment, seedbed treatment, mixing with culture soil, mixing with seedbed soil, mixing with a paste fertilizer, water surface treatment, spraying on water, etc., preferably seedling box treatment.

When the arthropod pest control composition of the present invention is applied to a plant or an area in which a plant is grown, the application amount varies depending on the kinds of plant to be protected, the species or population size of arthropod pest to be controlled, the form of a formulation, the timing of application, weather conditions, etc., but is generally within a range from 0.05 to 10,000 g, preferably from 0.5 to 1,000 g per 1,000 $m^2$ of an area where a plant is grown, in terms of the total amount of the present amide compound, the present anthranilamide compound and the Delphacidae control compound.

When the arthropod pest control composition of the present invention is applied to a rice seedling box, the application amount is generally within a range from 0.1 to 35 g, preferably from 0.2 to 20 g per one rice seedling box (width: about 60 cm, length: about 30 cm), in terms of the total amount of the present amide compound, the present anthranilamide compound and the Delphacidae control compound.

When the arthropod pest control composition of the present invention is applied to 20 rice seedling boxes per 1,000 $m^2$ of an area where rice is grown after transplantation, the application amount is generally within a range from 2 to 700 g, preferably from 4 to 400 g per 1,000 $m^2$ of an area where rice is grown after transplantation, in terms of the total amount of the present amide compound, the present anthranilamide compound and the Delphacidae control compound.

When the arthropod pest control composition of the present invention is applied to the seeds of plants, the application amount varies depending on the kinds of plant to be protected, the species or population size of arthropod pest to be controlled, the form of a formulation, the timing of application, weather conditions, etc., but is generally within a range from 0.001 to 100 g, preferably from 0.05 to 50 g per 1 kg of the seeds, in terms of the total amount of the present amide compound, the present anthranilamide compound and the Delphacidae control compound.

The arthropod pest control composition of the present invention in the form of an emulsifiable concentrate, a wettable powder or a suspension concentrate is generally applied after dilution with water. In this case, the total concentration of the present amide compound, the present anthranilamide compound and the Delphacidae control compound is generally 0.00001 to 10% by weight, preferably 0.0001 to 5% by weight. The arthropod pest control composition of the present invention in the form of a dust or a granule is generally applied as it is without dilution.

The arthropod pest control composition of the present invention may be applied to rice or an area in which rice is grown at the time, for example, before, during or after sowing or transplanting of rice. The timing of application may vary depending on the growing conditions of rice, the degree of occurrence of diseases, pests and weeds, weather conditions, etc., but is generally within a range from 30 days before sowing of rice to 20 days after transplanting of rice, preferably before sowing to before transplanting, more preferably 3 days before transplanting to before transplanting.

EXAMPLES

Hereinafter, the present invention will be described in more detail with reference to Formulation Examples and Test Examples, but not limited thereto. In the Examples, the term "part(s)" means part(s) by weight unless otherwise specified.

Firstly, Formulation Examples will be shown below.

Formulation Example 1

Two (2) parts of the present amide compound, 0.75 parts of the present anthranilamide compound (I), 1.5 parts of clothianidin, 1 part of synthetic hydrated silicon oxide, 2 parts of calcium lignosulfonate, 30 parts of bentonite and the rest parts of kaolin clay are mixed, and then 100 parts of the mixture is finely-ground and mixed. To the resultant mixture is added water. After that, the mixture is sufficiently kneaded and then dried while grinding to obtain granules.

Formulation Examples 2 to 11

The same procedure as described in Formulation Example 1 is repeated, except that each used amount of each compound as shown in Table 1 is used instead of 1.5 parts of clothianidin, to obtain each of the target granules.

TABLE 1

| Formulation Example | Compound | Used amount [part] |
|---|---|---|
| 2 | Imidacloprid | 2 |
| 3 | Thiamethoxam | 2 |
| 4 | Thiamethoxam | 8 |
| 5 | Dinotefuran | 2 |
| 6 | Fipronil | 1 |
| 7 | Pymetrozine | 3 |
| 8 | Present compound (I) | 2 |
| 9 | Present compound (I) | 8 |
| 10 | Present compound (II) | 2 |
| 11 | Present compound (II) | 8 |

Formulation Example 12

Two (2) parts of the present amide compound, 0.75 parts of the present anthranilamide compound (ii), 1.5 parts of clothianidin, 1 part of synthetic hydrated silicon oxide, 2 parts of calcium lignosulfonate, 30 parts of bentonite and the rest parts of kaolin clay are mixed, and then 100 parts of the mixture is finely-ground and mixed. To the resultant mixture is added water. After that, the mixture is sufficiently kneaded and then dried while grinding to obtain granules.

Formulation Examples 13 to 22

The same procedure as described in Formulation Example 12 is repeated, except that each used amount of each compound as shown in Table 2 is used instead of 1.5 parts of clothianidin, to obtain each of the target granules.

TABLE 2

| Formulation Example | Compound | Used amount [part] |
|---|---|---|
| 13 | Imidacloprid | 2 |
| 14 | Thiamethoxam | 2 |
| 15 | Thiamethoxam | 8 |
| 16 | Dinotefuran | 2 |
| 17 | Fipronil | 1 |
| 18 | Pymetrozine | 3 |
| 19 | Present compound (I) | 2 |
| 20 | Present compound (I) | 8 |

TABLE 2-continued

| Formulation Example | Compound | Used amount [part] |
|---|---|---|
| 21 | Present compound (II) | 2 |
| 22 | Present compound (II) | 8 |

Formulation Example 23

Three (3) parts of the present amide compound, 15 parts of the present anthranilamide compound (i) and 15 parts of clothianidin are added to a mixture of 4 parts of sodium lauryl sulfate, 2 parts of calcium lignosulfonate, 20 parts of a fine powder of synthetic hydrated silicon oxide and 41 parts of diatomaceous earth, and then the resultant mixture is sufficiently mixed with stirring to obtain a wettable powder.

Formulation Examples 24 to 30

The same procedure as described in Formulation Example 23 is repeated, except that each used amount of each compound as shown in Table 3 is used instead of 15 parts of clothianidin, to obtain each of the target wettable powders.

TABLE 3

| Formulation Example | Compound | Used amount [part] |
|---|---|---|
| 24 | Imidacloprid | 15 |
| 25 | Thiamethoxam | 15 |
| 26 | Dinotefuran | 15 |
| 27 | Fipronil | 15 |
| 28 | Pymetrozine | 15 |
| 29 | Present compound (I) | 15 |
| 30 | Present compound (II) | 15 |

Formulation Example 31

Three (3) parts of the present amide compound, 15 parts of the present anthranilamide compound (ii) and 15 parts of clothianidin are added to a mixture of 4 parts of sodium lauryl sulfate, 2 parts of calcium lignosulfonate, 20 parts of a fine powder of synthetic hydrated silicon oxide and 41 parts of diatomaceous earth, and then the resultant mixture is sufficiently mixed with stirring to obtain a wettable powder.

Formulation Examples 32 to 38

The same procedure as described in Formulation Example 31 is repeated, except that each used amount of each compound as shown in Table 4 is used instead of 15 parts of clothianidin, to obtain each of the target wettable powders.

TABLE 4

| Formulation Example | Compound | Used amount [part] |
|---|---|---|
| 32 | Imidacloprid | 15 |
| 33 | Thiamethoxam | 15 |
| 34 | Dinotefuran | 15 |
| 35 | Fipronil | 15 |
| 36 | Pymetrozine | 15 |

TABLE 4-continued

| Formulation Example | Compound | Used amount [part] |
| --- | --- | --- |
| 37 | Present compound (I) | 15 |
| 38 | Present compound (II) | 15 |

Formulation Example 39

One (1) part of the present amide compound, 0.5 parts of the present anthranilamide compound (i), 0.15 parts of clothianidin, 10 parts of talc and the rest parts of kaolin clay are finely-ground and mixed to obtain 100 parts of dusts.

Formulation Examples 40 to 47

The same procedure as described in Formulation Example 39 is repeated, except that each used amount of each compound as shown in Table 5 is used instead of 0.15 parts of clothianidin, to obtain 100 parts of each of the target dusts.

TABLE 5

| Formulation Example | Compound | Used amount [part] |
| --- | --- | --- |
| 40 | Clothianidin | 0.5 |
| 41 | Imidacloprid | 0.25 |
| 42 | Thiamethoxam | 0.35 |
| 43 | Dinotefuran | 0.35 |
| 44 | Fipronil | 0.25 |
| 45 | Pymetrozine | 0.25 |
| 46 | Present compound (I) | 0.35 |
| 47 | Present compound (II) | 0.35 |

Formulation Example 48

One (1) part of the present amide compound, 0.5 parts of the present anthranilamide compound (ii), 0.15 parts of clothianidin, 10 parts of talc and the rest parts of kaolin clay are finely-ground and mixed to obtain 100 parts of dusts.

Formulation Examples 49 to 56

The same procedure as described in Formulation Example 48 is repeated, except that each used amount of each compound as shown in Table 6 is used instead of 0.15 parts of clothianidin, to obtain 100 parts of each of the target dusts.

TABLE 6

| Formulation Example | Compound | Used amount [part] |
| --- | --- | --- |
| 49 | Clothianidin | 0.5 |
| 50 | Imidacloprid | 0.25 |
| 51 | Thiamethoxam | 0.35 |
| 52 | Dinotefuran | 0.35 |
| 53 | Fipronil | 0.25 |
| 54 | Pymetrozine | 0.25 |
| 55 | Present compound (I) | 0.35 |
| 56 | Present compound (II) | 0.35 |

Formulation Example 57

Ten (10) parts of the present amide compound, 2 parts of the present anthranilamide compound (i), 6.6 parts of clothianidin, 30 parts of white carbon containing 50 parts of ammonium polyoxyethylene alkylether sulfate and the rest parts of water are mixed, and then 100 parts of the resultant mixture is finely-ground by a wet grinding method to obtain a suspension concentrate.

Formulation Examples 58 to 65

The same procedure as described in Formulation Example 57 is repeated, except that each used amount of each compound as shown in Table 7 is used instead of 6.6 parts of clothianidin, to obtain each of the suspension concentrates.

TABLE 7

| Formulation Example | Compound | Used amount [part] |
| --- | --- | --- |
| 58 | Imidacloprid | 8 |
| 59 | Thiamethoxam | 8 |
| 60 | Dinotefuran | 5 |
| 61 | Dinotefuran | 10 |
| 62 | Fipronil | 5 |
| 63 | Pymetrozine | 10 |
| 64 | Present compound (I) | 8 |
| 65 | Present compound (II) | 8 |

Formulation Example 66

Ten (10) parts of the present amide compound, 2 parts of the present anthranilamide compound (ii), 6.6 parts of clothianidin, 30 parts of white carbon containing 50 parts of ammonium polyoxyethylene alkylether sulfate and the rest parts of water are mixed, and then 100 parts of the resultant mixture is finely-ground by a wet grinding method to obtain a suspension concentrate.

Formulation Examples 67 to 74

The same procedure as described in Formulation Example 66 is repeated, except that each used amount of each compound as shown in Table 8 is used instead of 6.6 parts of clothianidin, to obtain each of the suspension concentrates.

TABLE 8

| Formulation Example | Compound | Used amount [part] |
| --- | --- | --- |
| 67 | Imidacloprid | 8 |
| 68 | Thiamethoxam | 8 |
| 69 | Dinotefuran | 5 |
| 70 | Dinotefuran | 10 |
| 71 | Fipronil | 5 |
| 72 | Pymetrozine | 10 |
| 73 | Present compound (I) | 8 |
| 74 | Present compound (II) | 8 |

The effects of the present invention will be demonstrated below with reference to Test Examples.

Test Example 1

Each 10 mg of the present amide compound, the present anthranilamide compound (i), the present anthranilamide compound (ii), dinotefuran, the present compound (I) and the present compound (II) was dissolved in 0.2 ml of a 5% (w/v) solution of SORGEN TW-20 (manufactured by Dai-ichi Kogyo Seiyaku Co., Ltd.) in acetone (manufactured by Wako Pure Chemical Industries, Ltd.) and then diluted with water containing 0.02% by volume of a spreading agent [product name: Dain (registered trademark), manufactured by Sumitomo chemical garden products inc.] to a given concentration.

The water dilution of the present amide compound, the water dilution of the present anthranilamide compound (i) or the present anthranilamide compound (ii), the water dilution of dinotefuran and the water dilution of the present compound (I) or the present compound (II) were mixed to prepare a test solution.

Each the test solution was sprayed onto a rice seedling (*Oryza sativa*, cultivar: Hoshinoyume) at the 2.5 leaf stage grown in a paper pot in an amount of 10 ml per a seedling. This rice seedling was air-dried and then put into a glass test tube (diameter: 30 mm, height: 200 mm) with 4.8 ml of water. Into the test tube were released 10 third-instar nymphs of *Nilaparvata lugens*, and then the tube was placed in a room (25° C., humidity 55%). This is called a treated-section.

In the same manner as in the treated-section, a rice seedling without any treatment with the test solution was put into a glass test tube and then the insects were released thereto. This is called an untreated-section.

Five (5) days after releasing the tested nymphs, the insects were observed for life or death. From the observation results, an insect death rate was calculated by the following Equation 1) and a corrected insect death rate was calculated by the following Equation 2). For each treatment, there were 2 replicates. The average values are shown in Table 9.

Insect death rate (%)=(Number of tested insects−number of surviving insects)/Number of tested insects×100    Equation 1);

Corrected insect death rate (%)={(Insect death rate in treated section−Insect death rate in untreated section)/(100−Insect death rate in untreated section)}×100    Equation 2);

TABLE 9

| Comp. No. | Test compound | Concentration [ppm] | Corrected insect death rate [%] |
|---|---|---|---|
| 1 | Present amide compound | 3 | 100 |
|  | Present anthranilamide compound (i) | 1 |  |
|  | Dinotefuran | 3 |  |
| 2 | Present amide compound | 3 | 100 |
|  | Present anthranilamide compound (i) | 1 |  |
|  | Present compound (I) | 3 |  |
| 3 | Present amide compound | 3 | 100 |
|  | Present anthranilamide compound (i) | 1 |  |
|  | Present compound (II) | 3 |  |
| 4 | Present amide compound | 3 | 100 |
|  | Present anthranilamide compound (ii) | 1 |  |
|  | Dinotefuran | 3 |  |
| 5 | Present amide compound | 3 | 100 |
|  | Present anthranilamide compound (ii) | 1 |  |
|  | Present compound (I) | 3 |  |
| 6 | Present amide compound | 3 | 100 |
|  | Present anthranilamide compound (ii) | 1 |  |
|  | Present compound (II) | 3 |  |

Test Example 2

Each 10 mg of the present amide compound, the present anthranilamide compound (i), the present anthranilamide compound (ii), dinotefuran, the present compound (I) and the present compound (II) was dissolved in 0.2 ml of a 5% (w/v) solution of SORGEN TW-20 (manufactured by Dai-ichi Kogyo Seiyaku Co., Ltd.) in acetone (manufactured by Wako Pure Chemical Industries, Ltd.) and then diluted with water to a given concentration.

The water dilution of the present amide compound, the water dilution of the present anthranilamide compound (i) or the present anthranilamide compound (ii), the water dilution of dinotefuran and the water dilution of the present compound (I) or the present compound (II) were mixed to prepare a test solution.

Each 0.6 ml of the test solutions was sprayed onto a soil in the vicinity of the foot of a rice seedling (*Oryza sativa*, cultivar: Hoshinoyume) at the 2.5 leaf stage grown in a paper pot. After standing for 2 hours, the seedling was transplanted to a flooded soil in 1/10,000 a Wagner pot and then the pot was placed in a greenroom (23° C.). One (1) day after the treatment, the foot of the seedling was covered by a plastic cup and 10 third-instar nymphs of *Nilaparvata lugens* were released thereto. This is called a treated-section.

In the same manner as in the treated-section, a rice seedling without any treatment with the test solution was transplanted and then the insects were released thereto. This is called an untreated-section.

Six (6) days after releasing the tested nymphs, the insects were observed for life or death. From the observation results, an insect death rate was calculated by the following Equation 3) and a corrected insect death rate was calculated by the following Equation 4). For each treatment, there were 2 replicates. The average values are shown in Table 10.

Insect death rate (%)=(Number of tested insects−number of surviving insects)/Number of tested insects×100    Equation 3);

Corrected insect death rate (%)={(Insect death rate in treated section−Insect death rate in untreated section)/(100−Insect death rate in untreated section)}×100    Equation 4);

TABLE 10

| Comp. No. | Test compound | Application amount [mg/seedling] | Corrected insect death rate [%] |
|---|---|---|---|
| 7 | Present amide compound | 0.5 | 100 |
|  | Present anthranilamide compound (i) | 0.1875 |  |
|  | Dinotefuran | 0.5 |  |
| 8 | Present amide compound | 0.5 | 100 |
|  | Present anthranilamide compound (i) | 0.1875 |  |
|  | Present compound (I) | 1 |  |
| 9 | Present amide compound | 0.5 | 100 |
|  | Present anthranilamide compound (i) | 0.1875 |  |
|  | Present compound (II) | 1 |  |
| 10 | Present amide compound | 0.5 | 100 |
|  | Present anthranilamide compound (ii) | 0.1875 |  |
|  | Dinotefuran | 0.5 |  |
| 11 | Present amide compound | 0.5 | 100 |
|  | Present anthranilamide compound (ii) | 0.1875 |  |
|  | Present compound (I) | 1 |  |

TABLE 10-continued

| Comp. No. | Test compound | Application amount [mg/seedling] | Corrected insect death rate [%] |
|---|---|---|---|
| 12 | Present amide compound | 0.5 | 100 |
|  | Present anthranilamide compound (ii) | 0.1875 |  |
|  | Present compound (II) | 1 |  |

Test Example 3

Each 10 mg of the present amide compound, the present anthranilamide compound (i), the present anthranilamide compound (ii) and pymetrozine was dissolved in 0.2 ml of a 5% (w/v) solution of SORGEN TW-20 (manufactured by Dai-ichi Kogyo Seiyaku Co., Ltd.) in acetone (manufactured by Wako Pure Chemical Industries, Ltd.) and then diluted with water to a given concentration.

The water dilution of the present amide compound, the water dilution of the present anthranilamide compound (i) or the present anthranilamide compound (ii), and the water dilution of pymetrozine were mixed to prepare a test solution.

Each 0.6 ml of the test solutions was sprayed onto a soil in the vicinity of the foot of a rice seedling (*Oryza sativa*, cultivar: Hoshinoyume) at the 2.5 leaf stage grown in a paper pot. After standing for 2 hours, the seedling was transplanted to a flooded soil in 1/10,000 a Wagner pot and then the pot was placed in a greenroom (23° C.). Two (2) days after the treatment, the foot of the seedling was covered by a plastic cup and 5 adults of *Nilaparvata lugens* were released thereto. This is called a treated-section.

In the same manner as in the treated-section, a rice seedling without any treatment with the test solution was transplanted and then the insects were released thereto. This is called an untreated-section.

Three (3) days after releasing the insects, they were removed. Ten (10) days after releasing the insects, the number of freshly-hatched nymphs parasitizing rice was examined. From the observation results, a control value was calculated by the following Equation 5). For each treatment, there were 2 replicates. The average values are shown in Table 11.

Control value={1−(number of insects in treated section/number of insects in untreated section)}×100    Equation 5);

TABLE 11

| Comp. No. | Test compound | Application amount [mg/seedling] | Control value |
|---|---|---|---|
| 13 | Present amide compound | 1 | 94 |
|  | Present anthranilamide compound (i) | 0.375 |  |
|  | Pymetrozine | 1.5 |  |
| 14 | Present amide compound | 1 | 93 |
|  | Present anthranilamide compound (ii) | 0.375 |  |
|  | Pymetrozine | 1.5 |  |

Test Example 4

Each 10 mg of the present amide compound, the present anthranilamide compound (i), the present anthranilamide compound (ii) and pymetrozine was dissolved in 0.2 ml of a 5% (w/v) solution of SORGEN TW-20 (manufactured by Dai-ichi Kogyo Seiyaku Co., Ltd.) in acetone (manufactured by Wako Pure Chemical Industries, Ltd.) and then diluted with water to a given concentration.

The water dilution of the present amide compound, the water dilution of the present anthranilamide compound (i) or the present anthranilamide compound (ii) and the water dilution of pymetrozine were mixed to prepare a test solution.

Each 0.6 ml of test solution was applied to a soil in the vicinity of the foot of a rice seedling (*Oryza sativa*, cultivar: Hoshinoyume) at the 2.5 leaf stage grown in a paper pot. After standing for 2 hours, the seedling was transplanted to a flooded soil in 1/10,000 a Wagner pot and then the pot was placed in a greenroom (23° C.). Five (5) days after the treatment, the foot of the seedling was covered by a plastic cup and 10 third-instar nymphs of *Chilo suppressalis* were released thereto. This is called a treated-section.

In the same manner as in the treated-section, a rice seedling without any treatment with the test solution was transplanted and then the insects were released thereto. This is called an untreated-section.

Three (3) days after releasing the tested nymphs, the insects were observed for life or death. From the observation results, an insect death rate was calculated by the following Equation 6) and a corrected insect death rate was calculated by the following Equation 7). For each treatment there were 2 replicates. The average values are shown in Table 12.

Insect death rate (%)=(Number of tested insects−number of surviving insects)/Number of tested insects×100    Equation 6);

Corrected insect death rate (%)={(Insect death rate in treated section−Insect death rate in untreated section)/(100−Insect death rate in untreated section)}×100    Equation 7);

TABLE 12

| Comp. No. | Test compound | Application amount [mg/seedling] | Corrected insect death rate [%] |
|---|---|---|---|
| 15 | Present amide compound | 0.5 | 100 |
|  | Present anthranilamide compound (i) | 0.1875 |  |
|  | Pymetrozine | 0.75 |  |
| 16 | Present amide compound | 0.5 | 100 |
|  | Present anthranilamide compound (ii) | 0.1875 |  |
|  | Pymetrozine | 0.75 |  |

The invention claimed is:

1. An arthropod pest control composition comprising an amide compound represented by formula (1):

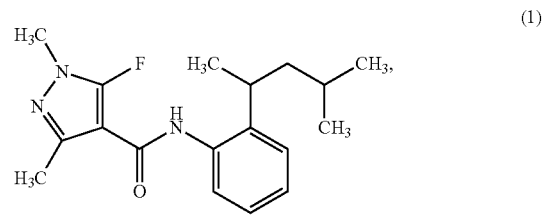 [SMILES: Cc1nn(C)c(F)c1C(=O)Nc1ccccc1C(C)CC(C)C]

an anthranilamide compound represented by formula (2):

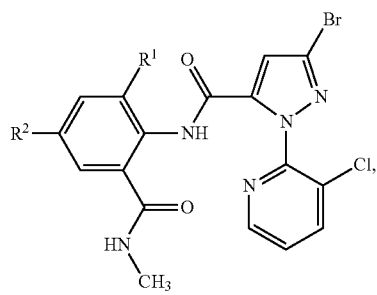

wherein a combination of $R^1$ and $R^2$ represents a combination wherein $R^1$ is a methyl group and $R^2$ is a chlorine atom, or a combination wherein $R^1$ is a methyl group and $R^2$ is a cyano group, and
one or more Delphacidae control compounds selected from the following group (A):
Group (A): a group consisting of clothianidin, imidacloprid, thiamethoxam, and a compound represented by formula (II):

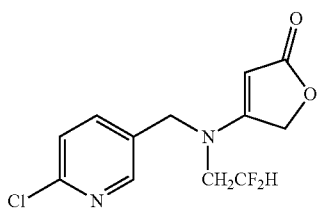

wherein the weight ratio of the amide compound to the anthranilamide compound is from 5:1 to 1:5, and the weight ratio of the amide compound to the Delphacidae control compound is from 4:1 to 1:5.

2. A method for controlling an arthropod pest, which comprises applying an effective amount of the arthropod pest control composition according to claim 1 to a plant or an area in which a plant is grown.

3. The method for controlling an arthropod pest according to claim 2, wherein the plant or the area in which a plant is grown is rice or area in which rice is grown.

4. The arthropod pest control composition according to claim 1, wherein in the compound represented by formula (2), $R^1$ is a methyl group and $R^2$ is a cyano group.

5. The arthropod pest control composition according to claim 1, wherein the Delphacidae control compound is a compound represented by formula (II):

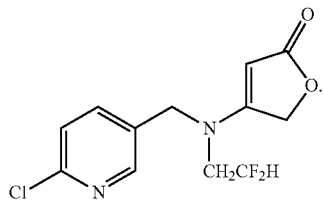

6. The arthropod pest control composition according to claim 1, wherein in the compound represented by formula (2), $R^1$ is a methyl group and $R^2$ is a cyano group, and the Delphacidae control compound is a compound represented by formula (II):

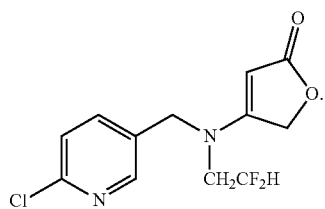

* * * * *